United States Patent [19]

Schucker

[11] Patent Number: 5,430,224
[45] Date of Patent: Jul. 4, 1995

[54] SUPERCRITICAL PERSTRACTION PROCESS

[75] Inventor: Robert C. Schucker, Baton Rouge, La.

[73] Assignee: Exxon Research & Engineering Company, Florham Park, N.J.

[21] Appl. No.: 228,483

[22] Filed: Apr. 15, 1994

[51] Int. Cl.⁶ .................. C07C 7/144; B01D 11/00
[52] U.S. Cl. ...................... 585/818; 585/819; 210/644; 210/648; 210/650
[58] Field of Search .............. 585/818, 819; 210/644, 210/648, 650

[56] References Cited

U.S. PATENT DOCUMENTS

| | | | |
|---|---|---|---|
| 2,940,920 | 6/1960 | Garwin | 208/45 |
| 2,980,602 | 4/1961 | Garwin | 208/45 |
| 4,125,459 | 11/1978 | Garwin | 208/309 |
| 4,239,616 | 12/1980 | Gearhart | 208/309 |
| 4,273,644 | 6/1981 | Harris et al. | 208/321 |
| 4,278,529 | 7/1981 | Garwin | 208/309 |
| 4,828,773 | 5/1989 | Feimer et al. | 264/45.5 |
| 4,879,044 | 11/1989 | Feimer et al. | 210/654 |
| 4,885,096 | 12/1989 | Black | 210/640 |
| 4,914,064 | 4/1990 | Schucker | 502/4 |
| 4,929,357 | 5/1990 | Schucker | 210/640 |
| 4,929,358 | 5/1990 | Koenitzer | 210/640 |
| 4,944,880 | 7/1990 | Ho et al. | 210/640 |
| 4,946,594 | 8/1990 | Thaler et al. | 210/651 |
| 4,976,868 | 12/1990 | Sartori et al. | 210/640 |
| 4,983,338 | 1/1991 | Schucker | 264/45.1 |
| 4,990,275 | 2/1991 | Ho et al. | 252/62.3 Q |
| 4,997,906 | 3/1991 | Thaler et al. | 528/272 |
| 5,039,418 | 8/1991 | Schucker | 210/640 |
| 5,055,631 | 10/1991 | Sartori et al. | 585/819 |
| 5,055,632 | 10/1991 | Schucker | 585/819 |
| 5,063,186 | 11/1991 | Schucker | 502/4 |
| 5,107,056 | 4/1992 | Chen et al. | 585/818 |
| 5,107,059 | 4/1992 | Chen et al. | 585/818 |
| 5,130,017 | 7/1992 | Schucker | 210/640 |

FOREIGN PATENT DOCUMENTS

| | | | |
|---|---|---|---|
| 1051115 | 2/1989 | Japan | B01D 37/00 |
| 2190398 | 11/1987 | United Kingdom | C10G 21/00 |

Primary Examiner—Anthony McFarlane
Assistant Examiner—Nhat D. Phan
Attorney, Agent, or Firm—Joseph J. Allocca

[57] ABSTRACT

A feed stream comprising a mixture of at least two separable components is separated into a permeate rich in one or more components and a retentate lean in those same components by a process comprising dissolving the feed in a supercritical solvent under supercritical conditions to produce a solution and contacting the solution with a dense, non-porous perstraction membrane having a first and a second surface, said contacting being along a first surface, wherein a portion of the feed dissolves into the first surface of the membrane, migrates through the perstraction membrane under a concentration gradient and emerges from the membrane at the second surface, as a permeate, the permeate being removed from the second surface by use of a sweep fluid comprising a supercritical solvent at supercritical conditions which may be the same as or different from the supercritical solvent in which the feed is dissolved.

7 Claims, 5 Drawing Sheets

SUPERCRITICAL PERSTRACTION PROCESS

FIELD OF THE INVENTION

The present invention relates to the perstractive separation of a multicomponent feed stream into a distinct permeate stream rich in one or more components of the feed stream and a distinct retentate stream lean in those same components.

BACKGROUND OF THE INVENTION

The separation of mixed component feeds into a first fraction rich in one or more components of the feed and a second fraction lean in those same components has been long pursued by industry. Gross separations have been achieved by such procedures as distillation, solvent extraction, extractive distillation and, most recently, membrane separation. In each instance, the degree of separation achieved and the purity of the product recovered has risen as the sophistication of the process employed has improved and so long as the components separated possessed characteristic which facilitate their separation. Thus, while when the components of a mixed component feed possessed substantially similar boiling points distillation would be an inadequate separation procedure, separation could still be achieved if the components differed in terms of aromaticity, polarity or molecular size, etc. Such differences would make the feed amenable to separation by extraction, size dependent membrane separation (e.g., ultrafiltration or reverse osmosis) or solubility dependent membrane separation (e.g. perstraction or pervaporation).

Residual oils contain substantial quantities of molecules that are suitable for cat cracking; and separation of those components by various means has been the target of research for a number of years. The major focus has been in the reduction of metals and Con carbon in the fraction going to the cat cracker to minimize the effect of these species on catalyst activity and life.

Clearly, one way to accomplish a rough separation of this type is deasphalting using propane or mixed propane/butanes; however, this separation is not as clean as required and every refinery does not have a deasphalter.

Ultrafiltration using polymeric or ceramic membranes and reverse osmosis (both pressure-driven processes) have also been evaluated in recent years but to date have not been able to achieve the degree of separation needed to make the process attractive. Furthermore, it has been found that in ultrafiltration it is not the membrane that is actually doing the separation but rather a gel layer of larger molecules that forms on the surface of the membrane after a short time. This gel layer decreases the flux and is not very selective.

Concentration-driven membrane separation processes (pervaporation and perstraction) have been investigated in recent years for the separation of aromatic from non-aromatic species; and some testing has been done on heavier lube stocks. Results show clearly that diffusivity through the membrane decreases markedly (as does volatility) as molecular weight increases. Therefore, pervaporation is not feasible for residual oils and perstraction using conventional solvents also does not work very well for even heavier lube stocks.

Perstraction is a concentration-driven membrane process in which a liquid feed is contacted with one side of a non-porous membrane, whereupon a portion of the feed selectively dissolves into and then diffuses across the membrane. Removal of the permeate molecules from the downstream side of the membrane is accomplished by sweeping the membrane with a fluid that does not contain the permeating species. Therefore the concentration gradient that drives diffusion is maximized.

The importance of perstraction will arise not so much from the separation of light feeds (for which separation pervaporation can easily be used) but in the separation of heavier feeds—for example, the separation of aromatics from non-aromatics in jet fuel or diesel fuel or the separation of aromatics from coker naphthas and gas oils which contain diolefins which will oligimerize at higher pervaporation temperatures forming harmful gums, or the separation of non-asphaltenes (also called maltenes in the literature) from asphaltenes.

The use of solvents at condition at or above their critical temperature and pressure in selective extraction procedures is also well known and the subject of numerous patents, see: U.S. Pat. Nos. 2,980,602; 2,940,920; 4,125,459; 4,278,529; 4,239,616; 4,273,644.

THE PRESENT INVENTION

Multi component feed streams are separated into a first fraction enriched in one or more components of the feed stream and a second fraction lean in those same components by the process comprising dissolving the feed stream in a diluent solvent at or above its critical temperature and pressure to produce a solution or partial solution, feeding the solution to a perstraction membrane separation unit containing a dense, (i.e., non-porous) membrane having a first and a second surface, contacting the solution with the first surface of the perstractive membrane wherein one or more components of the feed present in the solution selectively dissolves in and permeates through the perstraction membrane under the influence of a concentration gradient and accumulates on the second surface of the membrane and is removed therefrom by use of a sweep fluid constituting a supercritical solvent which may be the same or different supercritical solvent, preferably the same, as used to dissolve the feed, and is at supercritical conditions, the sweep fluid removing the permeate from the second membrane surface thereby maintaining the concentration gradient driving force, recovering the permeate in sweep solvent solution and sending it to permeate recovery means wherein the permeate is separated or disengaged from the sweep solvent solution by adjusting the conditions over the solvents to below the critical temperature and pressure of the solvent or by raising the temperature at constant or only slightly increased pressure thereby lowering the density of the solvent and thus precipitating the permeate as a distinct second phase, separating the permeate phase from the solvent phase, adjusting the condition over the solvent to the original temperature and pressure of the solvent and recycling the supercritical solvent back to the process as sweep fluid. In general and typically there is a pressure gradient across the membrane (trans membrane pressure gradient) of less than about 50 psig, preferably less than about 25 psig, most preferably 0 psig.

Retentate laden solvent solution is recovered from the first surface of the membrane and sent to retentate recovery means for separating or disengaging the retentate from the solvent by changing the conditions over the solvent to below the critical temperature and pressure of the solvent or by increasing the temperature at constant or only slightly increased pressure wherein the retentate separates into a distinct phase from the solvent, separating the retentate phase from the solvent phase, readjusting conditions over the solvent to the original temperature and pressure of the solvent and recycling the solvent to the beginning of the process as feed diluent.

Solvents useful in the present invention are those solvents whose critical temperatures fall in the range 20° to 200° C., preferably 20° to 100° C., and whose critical pressures fall in the range 500 to 1500 psig, preferably 600 to 1100 psig and are a good solvent for at least a portion of the feed involved.

In general most of the solvents possessing these recited critical temperature and pressure characteristics are good solvents for some portion of the feed; as feeds get heavier, solubility goes down. The solvents which are particularly useful in this process are those selected from the group consisting of carbon dioxide, ethane, ethylene, propane, propylene, n-butane, isobutane, butenes, n-pentane and mixtures thereof.

Preferred solvents are those which have some plasticizing effect on the perstraction membrane, but such an influence is not critical. From 0.01 to 10 volumes of feed are dissolved per volume solvent, preferably 0.01 to 2.0 volumes of feed are dissolved per volume of solvent. At the higher dilution levels it is unlikely that many feeds will completely dissolve in the solvent; however, if feed and solvent are mixed together at high dilution ratios two phases will result when at least a portion of the feed dissolves in the supercritical solvent phase.

The feeds which can be separated by the present process include mixed organic fractions boiling above about 100° C., preferably above about 150° C. Typical feeds constitute mixture of aliphatic, aromatic, naphthenic, and heteroatomic cyclic and non-cyclic aromatic and non-aromatic molecules, preferably mixtures of aromatic (single and multi-ring aromatics and heteroatom containing aromatics) and non-aromatics. The preferred feeds are the heavier organic or hydrocarbon feeds, especially those wherein the components boil within the same, relatively narrow boiling range and differ from each other only in terms of aromaticity.

The process of the present invention is particularly well suited for the separation of components present in heavier, higher boiling organic fraction and hydrocarbon fractions such as jet fuel, diesel fuel, vacuum gas oil (cat feed), lube base stocks and residual oils. While some of these feeds can be separated into their components by pervaporation, such a process must employ temperatures which in most instances would have to exceed the operating temperature of currently available membranes in order to be economic. Perstraction, however, is a viable option for such separation and the present invention, and perstraction using a supercritical solvent greatly and unexpectedly enhances the operating attractiveness of perstraction.

Perstraction membranes used in the present invention are dense, (i.e., non-porous) membranes wherein the mechanism of permeation is solution-diffusion under the influence of a concentration gradient, rather than pressure driven/molecular size influenced separation as through porous membranes.

Perstraction membranes include polyurethane, polyurea/urethane, polycarbonate, polyimide, polyesterimide membranes, described and claimed in U.S. Pat. Nos. 4,976,868, 4,944,880, 4,990,275, 4,946,594, 4,997,906, 5,055,631, 4,885,096, 4,914,064, 5,063,186, 5,055,632, 5,130,017, 5,039,418, 4,929,357, 4,983,338, 4,929,358, 4,828,773, 4,879,044.

The membranes can be used in any convenient form such as sheets, tubes or hollow fibers. Sheets can be used to fabricate spiral wound modules familiar to those skilled in the art.

Alternatively, sheets can be used to fabricate a flat stack permeator comprising a multitude of membrane layers alternately separated by feed-retentate spacers and permeate spacers. The layers are glued along their edges to define separate feed-retentate zones and permeate zones. This device is described and claimed in U.S. Pat. No. 5,104,532.

Tubes can be used in the form of multi-leaf modules wherein each tube is flattened and placed in parallel with other flattened tubes. Internally each tube contains a spacer. Adjacent pairs of flattened tubes are separated by layers of spacer material. The flattened tubes with positioned spacer material is fitted into a pressure resistant housing equipped with fluid entrance and exit means. The ends of the tubes are clamped to create separate interior and exterior zones relative to the tubes in the housing. Apparatus of this type is described and claimed in U.S. Pat. No. 4,761,229.

Hollow fibers can be employed in bundle arrays potted at either end to form tube sheets and fitted into a pressure vessel thereby isolating the insides of the tubes from the outside of the tubes. Apparatus of this type are known in the art. A modification of the standard design, which was specifically designed for perstraction, involves dividing the hollow fiber bundle into separate zones by use of baffles which redirect fluid flow on the tube side of the bundle and prevent fluid channelling and polarization on the tube side. This modification is disclosed and claimed in U.S. Pat. No. 5,169,530.

Preferably the direction of flow in a hollow fiber element will be counter-current or even transverse rather than co-current. The preferred counter-current flow can be achieved by wrapping the hollow fiber bundle in a spiral wrap of flow-impeding material. This spiral wrap extends from a central mandrel at the center of the bundle and spirals outward to the outer periphery of the bundle. The spiral wrap contains holes along the top and bottom ends whereby fluid entering the bundle for tube side flow at one end is partitioned by passage through the holes and forced to flow parallel to the hollow fiber down the channel created by the spiral wrap. This flow direction is counter-current to the direction of flow inside the hollow fiber. At the bottom of the channels the fluid re-emerges from the hollow fiber bundle through the holes at the opposite end of the spiral wrap and is directed out of the module. This device is disclosed and claimed in U.S. Pat. No. 5,234,591.

Multiple Separation elements, be they spiral wound or hollow fiber elements can be employed either in series or in parallel. U.S. Pat. No. 5,238,563 discloses a multiple-element housing wherein the elements are grouped in parallel with a feed/retentate zone defined by a space enclosed by two tube sheets arranged at the same end of the element. The central mandrels of the elements pass through the feed/retentate zone space defined by the two tube sheets and empty permeate outside the defined space into a permeate collection zone from which it is removed, while the tube sheet directly attached to the element is in open relationship to the interior of the membrane element and retentate accumulates in the space between the top tube sheet and the bottom tube sheet from which it is removed.

The preferred membranes employed in the present invention are generally described as polyesterimide membranes and are described and claimed in U.S. Pat. Nos. 4,944,880 and 4,990,275.

The polyesterimide membranes are made from a copolymer comprising a polyimide segment and an oligomeric aliphatic polyester segment, the polyimide being derived from a dianhydride having between 8 and 20 carbons and a diamine having between 2 and 30 carbons and the oligomeric aliphatic polyester being a polyadipate, a polysuccinate, a polymalonate, a polyoxalate or a polyglutarate. Alternately, an activated anhydride acid such as teraphthalic anhydride acid chloride may be used.

The diamines which can be used include phenylene diamine, methylene dianiline (MDA), methylene di-o-chloroaniline (MOCA), methylene bis (dichloroaniline)(tetrachloro MDA), methylene dicyclohexylamine ($H_{12}$-MDA), methylene dichlorocyclohexylamine ($H_{12}$MOCA), methylene bis (dichlorocyclohexylamine)(tetrachloro $H_{12}$MDA), 4,4'-(hexafluoroisopropylidene)-bisaniline (6F diamine), 3,3'-diaminophenyl sulfone (3,3' DAPSON), 4,4'-diaminophenyl sulfone (4,4' DAPSON), 4,4'-dimethyl-3,3'-diaminophenyl sulfone (4,4'-dimethyl-3,3' DAPSON), 2,4-diamino cumene, methyl bis(di-o-toluidine), oxydianiline (ODA), bisaniline A, bisaniline M, bisaniline P, thiodianiline, 2,2-bis[4-(4-aminophenoxy)-phenyl]propane (BAPP), bis[4-(4-aminophenoxy phenyl)sulfone (BAPS), 4,4'-bis(4-aminophenoxy) biphenyl (BAPB), 1,4-bis(4-aminophenoxy)benzene (TPE-Q), and 1,3-bis(4-aminophenoxy)benzene (TPE-R).

The dianhydride is preferably an aromatic dianhydride and is most preferably selected from the group consisting of pyromellitic dianhydride, 3,3',4,4'-benzophenone tetracarboxylic dianhydride, 4,4'-(hexafluoroisopropylidene)-bis(phthalic anhydride), 4,4'-oxydiphthalic anhydride, diphenylsulfone-3,3'4,4'-tetracarboxylic dianhydride, and 3,3',4,4'-biphenyl-tetracarboxylic dianhydride.

Examples of preferred polyesters include polyethylene adipate and polyethylene succinate.

The polyesters used generally have molecular weights in the range of 500 to 4000, preferably 1000 to 2000.

In practice the membrane may be synthesized as follows. One mole of a polyester, e.g., polyadipate, polysuccinate, polyoxalate, polyglutarate or polymalonate, preferably polyethylene adipate or polyethylene succinate, is reacted with two moles of the dianhydride, e.g., pyromellitic dianhydride, to make a prepolymer in the endcapping step. One mole of this prepolymer is then reacted with one mole of diamine, e.g., methylene di-o-chloroaniline (MOCA) to make a copolymer. Finally, heating of the copolymer at 260°–300° C. for about ½ hour leads to the copolymer containing polyester and polyimide segments. The heating step converts the polyamic acid to the corresponding polyimide via imide ring closure with removal of water.

In the synthesis an aprotic solvent such as dimethylformamide (DMF) is used in the chain-extension step. DMF is a preferred solvent but other aprotic solvents are suitable and may be used. A concentrated solution of the polyamic acid/polyester copolymer in the solvent is obtained. This solution is used to cast the membrane. The solution is spread on a glass plate or a high temperature porous support backing, the layer thickness being adjusted by means of a casting knife. The membrane is first dried at room temperature to remove most of the solvent, then at 120° C. overnight. If the membrane is cast on a glass plate it is removed from the casting plate by soaking in water. If cast on a porous support backing it is left as is. Finally, heating the membrane at 300° C. for about 0.5 hours results in the formation of the polyimide. Obviously, heating to 300° C. requires that if a backing is used the backing be thermally stable, such as teflon, fiber glass, sintered metal or ceramic or high temperature polymer backing.

In the present process the feed to be separated is dissolved in the solvent maintained at or above its critical temperature and pressure. The feed component(s) which permeates through the membrane is (are) swept away from the permeate side surface of the membrane by use of a sweep fluid. This sweep fluid, by removing the permeated component from the permeate side surface of the membrane maintains the concentration gradient between the feed side and the permeate side of the membrane. It is this concentration gradient which constitutes the driving force for the separation process.

The sweep fluid used is also a solvent maintained at or above its critical pressure and temperature on the permeate side of the membrane. The supercritical solvent serving as the sweep fluid may be the same as or different from the supercritical solvent in which the feed is dissolved. Preferably it is the same supercritical solvent maintained under the same supercritical conditions as the solvent in which the feed is dissolved.

In the present perstraction process employing supercritical feed solvents and sweep fluids there is little or no transmembrane temperature or pressure gradient between the feed zone and the permeate zone and it is preferred that there be no transmembrane temperature or pressure gradient. The existence of any minor transmembrane temperature or pressure gradient is expected to have negligible impact. Gradients much higher than those normally encountered in supercritical solvent extraction processes would have to be present in order for them to have an effect on the present process.

In the process, the permeated fraction in the sweep fluid is recovered from the fluid by recovering the sweep fluid/permeated fraction solution from the membrane separation zone and sending it to a separate permeated fraction recovery zone wherein the conditions of temperature and/or pressure over the fluid are changed so as to result in a change in the solvent power of the fluid. As a consequence, the permeated fraction in the fluid separates out as a distinct phase which can be recovered by e.g., decantation, draining, etc. resulting in the recovery of a distinct permeate fraction stream and a distinct recovered sweep fluid stream. The recovered sweep fluid is recycled to the membrane separation zone after reapplication of supercritical temperature and/or pressure conditions.

In the same way, non-permeated species (retentate) remaining on the feed side of the membrane are separated from the supercritical dissolving solvent by sending it to a separate retentate fraction recovery zone wherein the conditions of temperature and/or pressure over the fluid are changed so as to result in a change in the solvent power of the fluid. The retentate fraction in the fluid separates out as a distinct phase which can be recovered by, e.g., decantation, drawing, etc. The solvent, free of retentate, is recycled after being returned to feed conditions.

Figure 1:
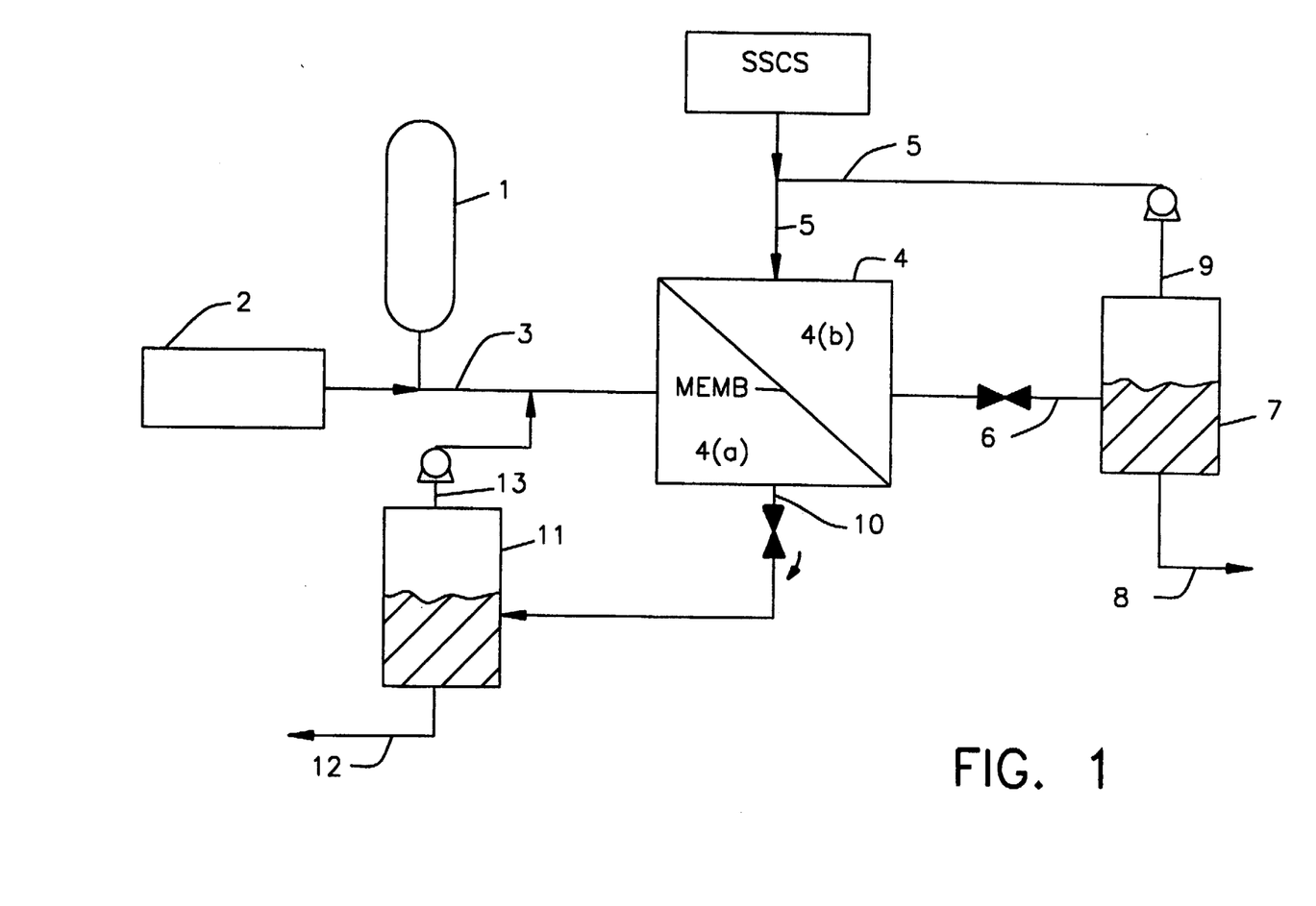
FIG. 1 is a schematic of a processing sequence for practicing the supercritical solvent perstractive process of the present invention.

This process illustrated by reference to FIG. 1.

Multi-component feed (1) is dissolved in supercritical solvent (2) in line 3 and fed via line (3) into membrane separation unit (4) at the feed side (4a) operation under perstraction condition. Sweep supercritical solvent (SSCS) is fed via line 5 into the membrane separation unit (4) at the permeate side (4b). One or more of the components present in the feed permeate through membrane (Memb) in unit 4 from feed side (4a) to permeate side (4b) and are removed from permeate side (4b) by the sweep solvent and sent via line 6 to permeate recovery zone 7 wherein the condition on the permeate/sweep fluid solution are changed to generate a phase change. The permeate phase separates from the sweep fluid and depending on the density is either the top or bottom phase. In the figure the permeate is shown as more dense and is recovered by draining from the bottom of zone 7 via line 8 while solvent is recovered via line 9 and sent, after re-application of feed condition and addition of any needed make up solvent, via line 5 back to the membrane unit 4 at permeate side (4b) for reuse as sweep fluid.

Retentate dissolved in supercritical solvent is received from membrane unit 4 from feed side 4a via line 10 and sent to retentate recovery unit 11 where the condition on the retentate/supercritical solvent solution are changed to result in the production of a two phase system whereby the retentate phase separates from the solvent. Again, depending on the retentate density, the retentate can be either the top or bottom phase. In the figure it is shown as the bottom phase and is recovered from zone 11 via line 12. Solvent is recovered from zone 11 via line 13 and following re-application of feed conditions is combined with first feed and make up supercritical solvent from (1) and (2) in line 3 and fed to membrane unit 4.

The invention is further described in the following nonlimiting examples and comparative examples.

The examples were conducted in a test cell set up such that the condition in the feed side and permeate side could be adjusted between supercritical and subcritical conditions.

During a test, a membrane would be mounted between the cell halves and fluid (n-heptane or $CO_2$) would be charged to both sides of the cell. The temperature and pressure were then adjusted to the desired values while fluid was circulated around each half with gear pumps. A sample loop containing a known quantity of diffusant (toluene) was located in the feed side loop and an ultraviolet detector was located in the permeate loop. To start a run, the sample loop was opened to the feed and sample was introduced instantaneously into the feed. Circulation was sufficient to create a well mixed cell feed half in 30 seconds. The permeate stream was then monitored for its UV absorbance at 254 nm (characteristic of aromatics). In this way, absorbance (which can be related to concentration) versus time of the diffusant in the permeate stream could be monitored.

Comparative Example 1

A polyesterimide (PEI) membrane on Teflon backing and about $7\mu$ thick, as described in U.S. Pat. Nos. 4,944,880 and 4,990,275 for pervaporative separation of aromatics from saturates, was mounted in the diffusion cell. The membrane was prepared by reacting 600 grams of polyethylene adipate (0.3117 mole) with 136.7 grams pyromellitic dianydride (0.627 mole) for 4 hours at 170° C. The reaction products were then diluted to 10% solids (by weight) with 50% acetone:50% DMF (by volume) and subsequently chain extended with 61.8 grams (0.31 mole) methylene dianiline. The product of this chain extension is a polyamic acid precursor. As the polymer solution thickened, it was further diluted with the same solvent mixture to a solids content of 4.5%. The solution was cast onto a microporous teflon support, solvent was dried off and the final film was cured at elevated temperatures (>200° C.) for a sufficient amount of time to imidize the polyamic acid precursor to the cyclic imide structure. Total cross-sectional area of the membrane was 14.55 cm$^2$ and total volume of each half of the cell was 67.94 cm$^3$. Both sides of the cell were filled with n-heptane (b.p. 98° C.) and the system was heated to 35° C. To start the run, approximately 0.08 cc toluene was injected into the feed stream and uv absorbance of the fluid on the permeate side was monitored as a function of time. This run represented permeation through a polymeric membrane in contact with a subcritical liquid. UV absorbance versus time data are presented in FIG. 2.

Example 1

Figure 2:
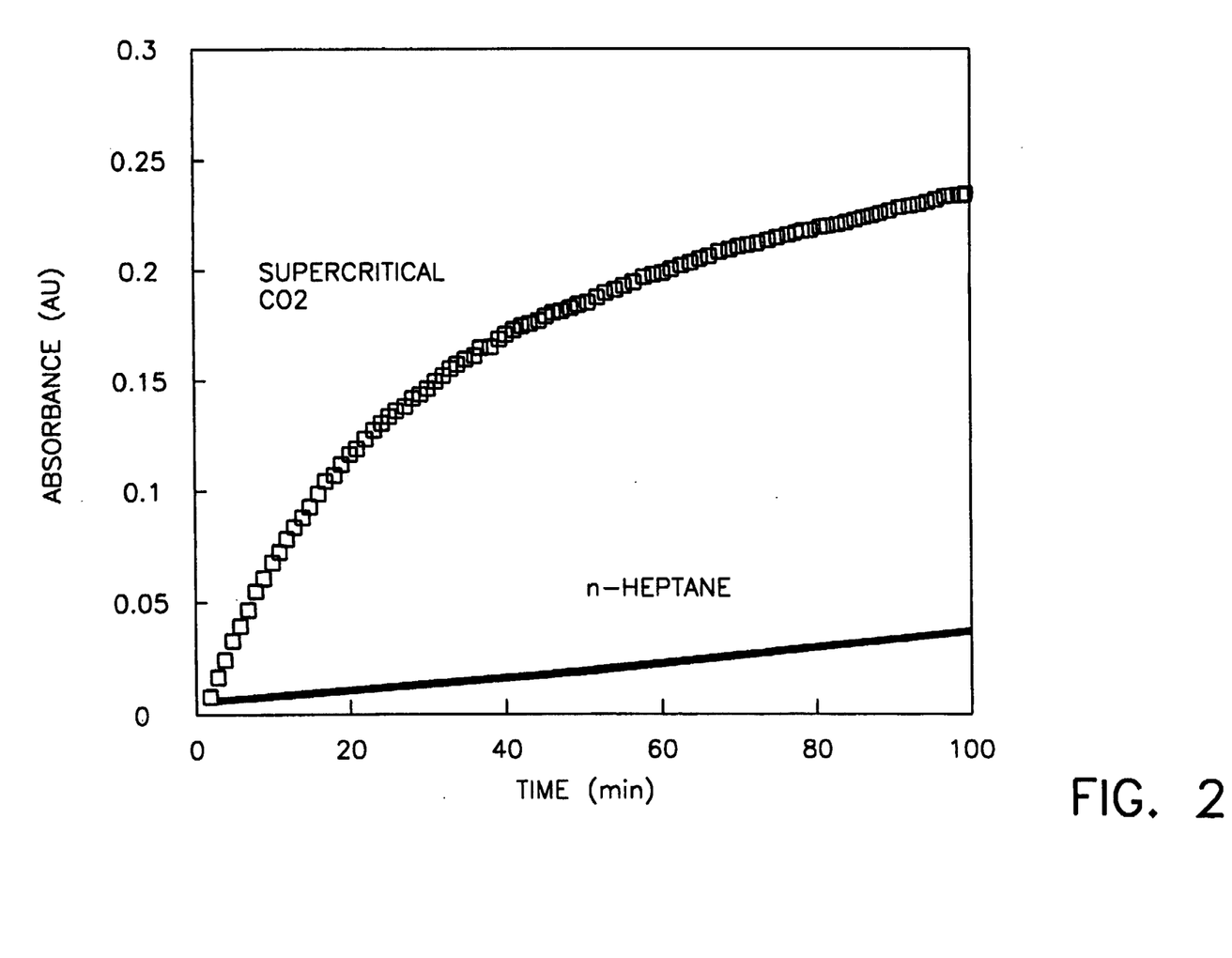
FIG. 2 compares the diffusion of toluene through a poly ester imide membrane at 35° C. when using supercritical solvent ($CO_2$) versus subcritical solvent (n-heptane).

This example was set up to directly compare permeation in the presence of a supercritical fluid versus that in subcritical liquid n-heptane. The membrane comprised the same piece of membrane used in Example 1; all conditions were the same as in Comparative Example 1 except that the fluid was supercritical $CO_2$ at 1200 psig instead of heptane. Results from this Example 1 are also shown in FIG. 2 labeled "supercritical $CO_2$". As can be seen, at a constant temperature of 35° C., permeation of toluene in the presence of supercritical $CO_2$ is substantially faster than in the presence of n-heptane. Initial slopes of the two curves show that the permeation is 26 times faster in the presence of supercritical $CO_2$.

Example 2

Figure 3:
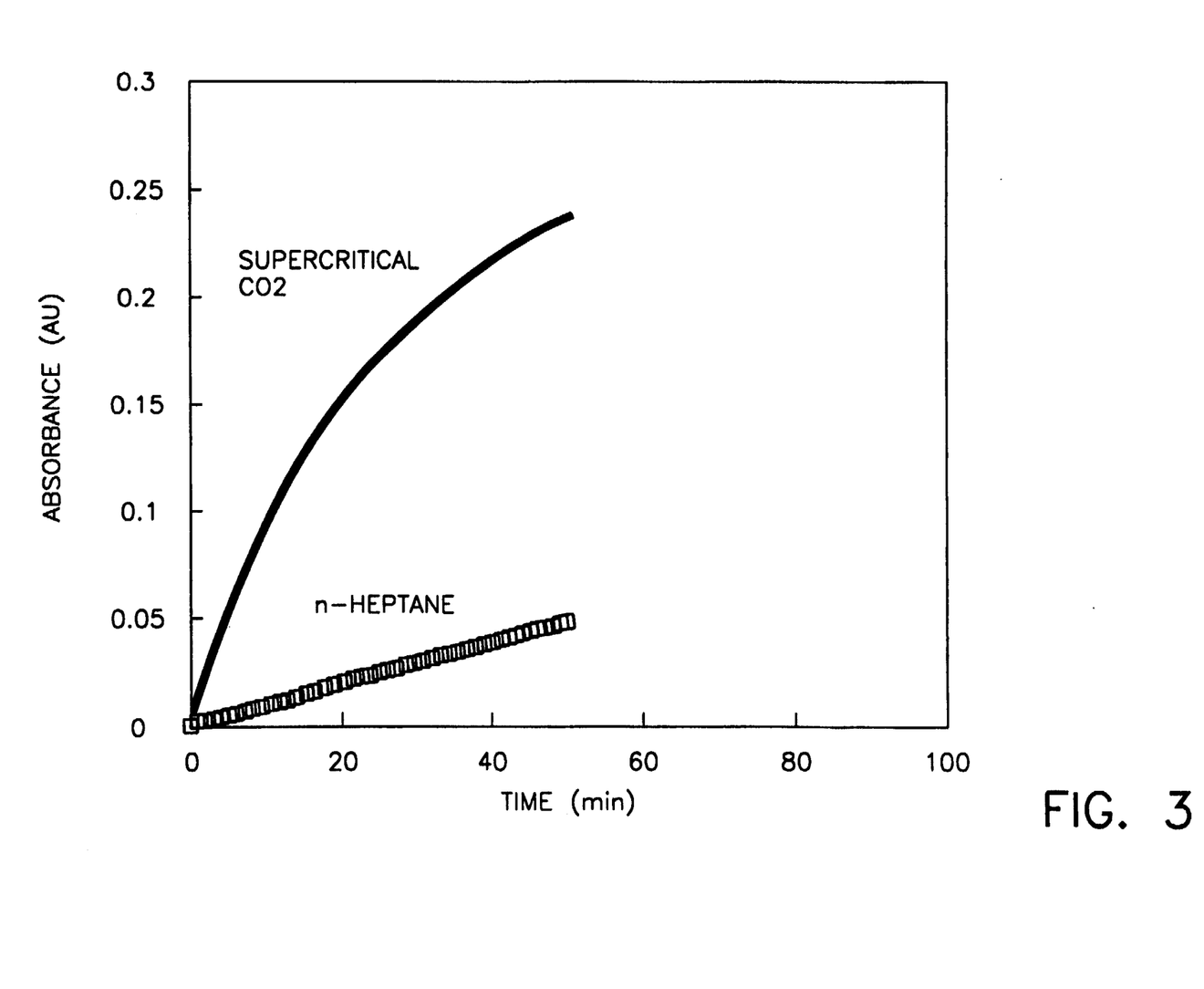
FIG. 3 compares the diffusion of toluene through a polyester imide membrane at 50° C. when using supercritical solvent ($CO_2$) versus subcritical solvent (n-heptane).

A third run was made with the same membrane essentially repeating Example 1 except that the temperature was 50° C. and the pressure of the supercritical $CO_2$ was 1650 psig in order to run at approximately the same density as Example 1. UV absorbance as a function of time for this run is shown in FIG. 3 labeled "Supercritical $CO_2$".

Comparative Example 2

A different but chemically and physically identical piece of the same membrane was used in Comparative Example 2 and the conditions in Comparative Example 1 with n-heptane as the solvent were repeated except that the temperature was held constant at 50° C. UV absorbance as a function of time is also plotted in FIG. 3 and labeled "n-Heptane". As can be seen again, permeation at 50° C. in the presence of supercritical $CO_2$ (Example 2) as the sweep fluid is significantly faster than permeation using subcritical n-heptane as the sweep fluid. Also, both of the permeation rates are faster at 50° C. than at 35° C. as expected due to the known temperature dependence of diffusivity.

Example 3 and Comparative Example 3

Figure 4:
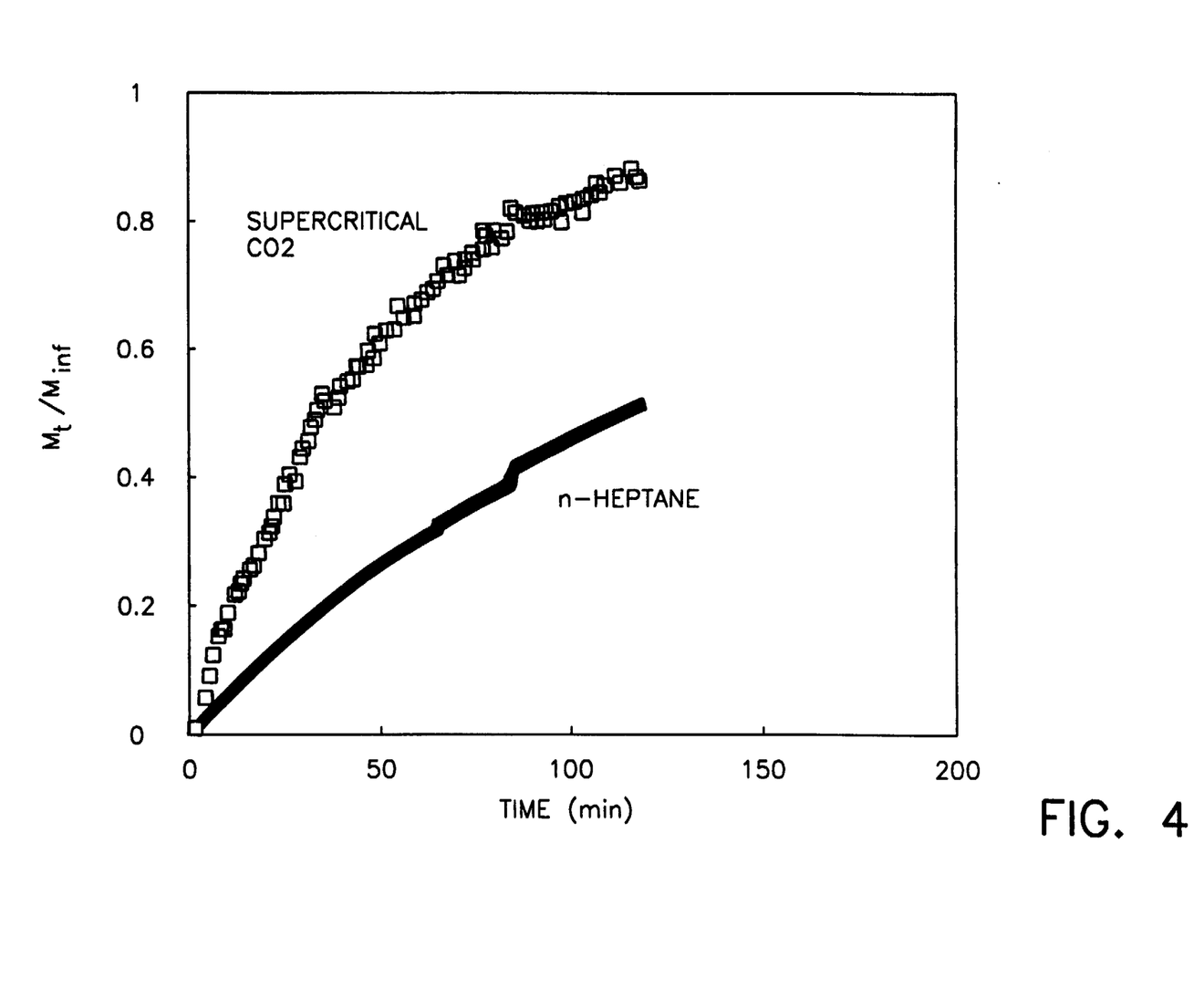
FIG. 4 compares the diffusion of toluene through a Latex Rubber membrane at 50° C. when using supercritical solvent ($CO_2$) versus subcritical solvent (n-heptane).

Identical runs to those carried out in Example 2 and Comparative Example 2 were carried out using a latex rubber membrane (cut from a surgical glove) approximately 194 microns thick. Results from those two runs are shown in FIG. 4. The data are presented in terms of $M_t/M_\infty$ (i.e., the amount of diffusant that had passed through the membrane at time, t, divided by the amount of permeate that had passed through the membrane at equilibrium). Once again, permeation in the presence of supercritical $CO_2$ is much faster than permeation in the presence of liquid n-heptane at the same temperature.

Example 4 and Comparative Example 4

Figure 5:
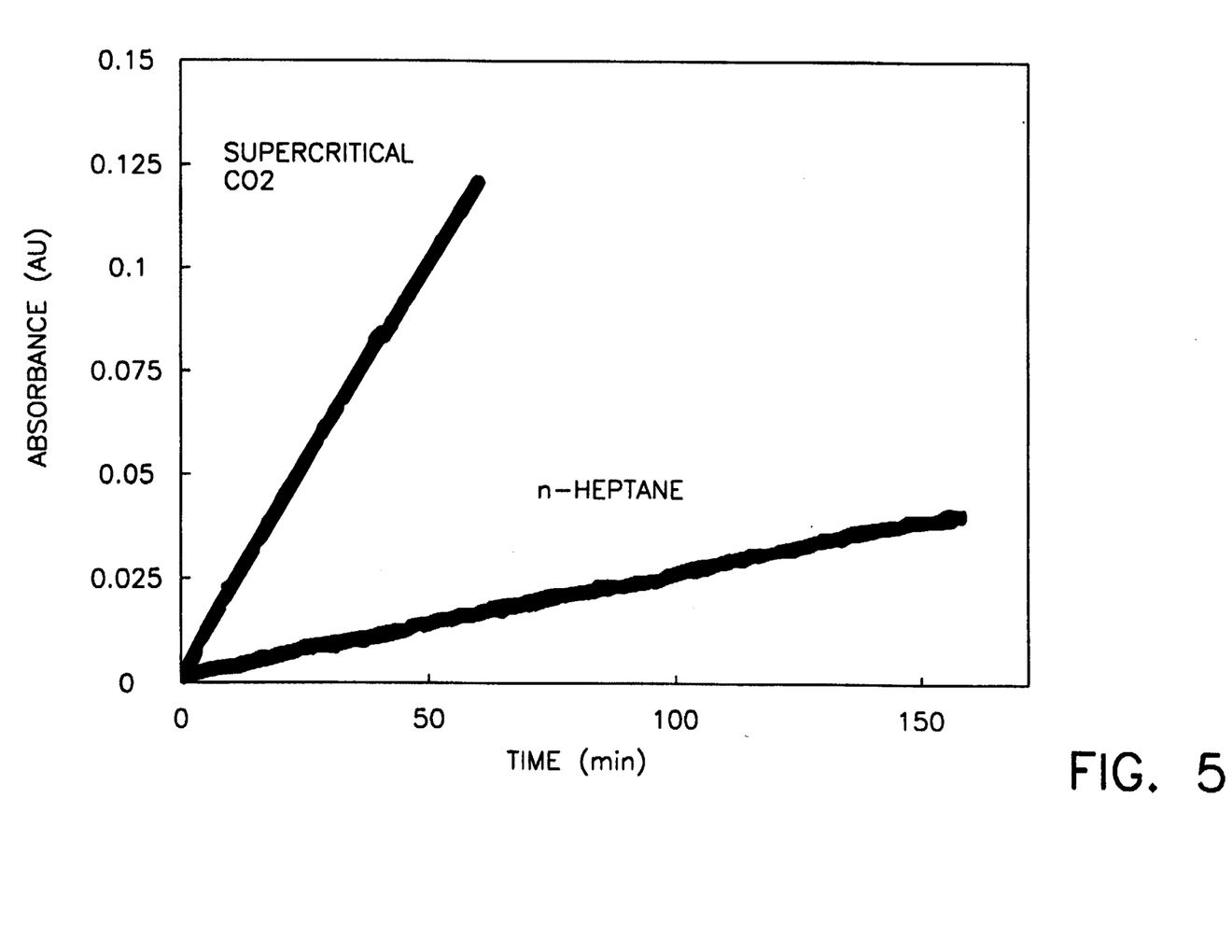
FIG. 5 compares the diffusion of toluene through a polyurea/urethane membrane at 50° C. when using supercritical solvent ($CO_2$) versus subcritical solvent (n-heptane).

Identical runs to those carried out in Example 3 and Comparative Example 3 were carried out using a polyurea/urethane membrane, made according to U.S. Pat. No. 4,914,064 issued on Apr. 3, 1990. The membrane was approximately 28 microns thick. Results from these two runs are shown in FIG. 5. Again, uv absorbance of the fluid on the permeate side of the membrane is plotted against time with a steeper slope indicating a faster rate of permeation. Measurement of the slopes of the two curves showed that the run carried out with supercritical $CO_2$ as the sweep permeated approximately 7.9 times faster than the run using n-heptane.

What is claimed is:

1. A process for the perstractive separation of a multi-component feed stream into a permeate stream rich in one or more components of the feed and a retentate stream lean in those same components comprising the steps of mixing the feed stream to be separated with a diluent solvent at or above its critical temperature and pressure to produce a solution, passing the solution to a membrane perstraction unit containing a dense membrane having a first and a second surface, contacting the solution with the first surface of the perstractive membrane wherein one or more components of the feed present in the solution selectively dissolve into and permeate through the perstraction membrane under the influence of a concentration gradient across the membrane maintained by the use of a sweep solvent maintained at or above its critical temperature and pressure along the second surface of the membrane said sweep solvent removing the components of the feed which permeate through the membrane and accumulate on the second surface, recovering the permeate in sweep solvent solution and sending it to permeate recovery means wherein the permeate is disengaged from the sweep solvent solution by reducing the density of the sweep solvent by adjusting the conditions of temperature and/or pressure and resulting in the permeate precipitating as a distinct second phase, separating the permeate phase from the sweep solvent phase, increasing the density of the sweep solvent by reapplication of the original conditions of temperature and/or pressure and recirculating the sweep solvent, recovering the retentate solution from the first surface of the membrane and sending it to retentate recovery means wherein the conditions of temperature and pressure on the diluent solution are adjusted to reduce the density of the diluent solvent to result in the retentate precipitating as a second phase which is separated from the diluent solvent phase, readjusting condition of temperature and pressure of the diluent solvent to their original levels and recirculating the diluent solvent to the beginning of the process wherein it is combined with fresh feed.

2. The process of claim 1 wherein the feed diluent solvent and the sweep solvent are different solvents.

3. The process of claim 1 wherein the feed diluent solvent and the sweep solvent are the same solvent.

4. The process of claim 1, 2 or 3 wherein the feed diluent solvents are solvents whose critical temperatures fall in the range 20° to 200° C. and whose critical pressures fall in the range 500 to 1500 psig.

5. The process of claim 4 wherein the feed diluent solvent and the sweep solvent are selected from carbon dioxide, ethane, ethylene, propane, propylene, n-butane, isobutane, butenes, n-pentane and mixtures thereof.

6. The process of claim 1, 2 or 3 wherein the feed to be separated is mixed organic fractions boiling above about 150° C.

7. The process of claim 6 wherein the feed to be separated is a mixture of aliphatic, aromatic, naphthenic and hetero-atomic cyclic and non-cyclic aromatic and non-aromatic molecules.

* * * * *